United States Patent [19]

Wu

[11] 4,147,726

[45] Apr. 3, 1979

[54] ACID-CATALYZED HYDROLYSIS OF ORGANIC HYDROPEROXIDE EMPLOYING A POLAR SOLVENT AND PHENOL AS REACTION MEDIUM

[75] Inventor: Yulin Wu, Bartlesville, Okla.

[73] Assignee: Phillips Petroleum Company, Bartlesville, Okla.

[21] Appl. No.: 739,905

[22] Filed: Nov. 8, 1976

[51] Int. Cl.$^2$ ................. C07C 37/08; C07C 45/00
[52] U.S. Cl. .................. 260/586 R; 260/464; 260/465 F; 260/465 G; 260/465 H; 260/465.6; 260/465.7; 260/465.8 R; 260/586 M; 260/590 R; 260/590 D; 260/591; 260/592; 260/593 A; 260/598; 260/599; 260/601 R; 260/601 H; 260/606; 568/569; 568/650; 568/741; 568/744; 568/747; 568/765; 568/768; 568/774; 568/780; 568/798
[58] Field of Search .......... 260/586 R, 621 C, 593 A, 260/592, 624 R, 610 B, 591, 590 R, 590 D, 464, 465 F, 465 G, 465 H, 465.6, 465.7, 465.8 R, 598, 599, 601 R, 601 H, 606

[56] References Cited

U.S. PATENT DOCUMENTS

| | | | |
|---|---|---|---|
| 2,430,865 | 11/1947 | Farkas et al. | 260/610 |
| 2,663,735 | 12/1953 | Filar et al. | 260/593 |
| 2,728,796 | 12/1955 | Vandinberg | 260/621 C |
| 2,734,085 | 2/1956 | Adams et al. | 260/593 |
| 3,948,995 | 4/1976 | Jouffret | 260/621 C |
| 3,978,141 | 8/1976 | Jouffret | 260/586 R |
| 4,021,490 | 5/1977 | Hudson | 260/621 C |

FOREIGN PATENT DOCUMENTS 740022  11/1955  United Kingdom ............. 260/586

*Primary Examiner*—Norman Morgenstern

[57] ABSTRACT

An organic hydroperoxide is hydrolyzed by acid-catalysis in a reaction medium comprising essentially a mixture of a polar solvent, e.g. a low boiling, low molecular weight alcohol and/or sulfolane and phenol. Specifically cyclohexanone and phenol are obtained from cyclohexylbenzene hydroperoxide.

12 Claims, No Drawings

ACID-CATALYZED HYDROLYSIS OF ORGANIC HYDROPEROXIDE EMPLOYING A POLAR SOLVENT AND PHENOL AS REACTION MEDIUM

This invention relates to the production of compounds by acid-catalyzed hydrolysis of an organic hydroperoxide. It also relates to such an operation conducted in a reaction medium comprising a polar solvent, e.g., a low boiling, low molecular weight alcohol and phenol. More specifically, the invention relates to the production of a cycloketone and phenol by the acid-catalyzed hydrolysis of an organic hydroperoxide in a reaction medium comprising essentially a low boiling, low molecular weight alcohol and phenol.

In one of its concepts, the invention provides a method for the acid-catalyzed hydrolysis of an organic hydroperoxide employing a reaction medium comprising essentially a mixture of a low boiling, low molecular weight alcohol (polar solvent) and phenol. In another of its concepts, the invention provides a method for producing cyclohexanone and phenol from cyclohexylbenzene by converting the cyclohexylbenzene to cyclohexylbenzene hydroperoxide and then hydrolyzing the latter by acid-catalysis, e.g., employing sulfuric acid in a reaction medium comprising essentially a low boiling, low molecular weight alcohol and phenol.

It is an object of this invention to produce a cyclic ketone. It is another object of the invention to produce phenol. A further object of the invention is to produce a cyclic ketone and a phenol from a phenyl-substituted alicyclic hydrocarbon, e.g., a naphthene, for example cyclohexylbenzene. It is a further object of the invention to considerably improve the yields of the ketone and the phenol which can be obtained. It is a further object of the invention to provide a reaction medium essentially comprising a mixture of solvents which will produce excellent yields of both the ketone and the phenol.

Other aspects, concepts, objects and the several advantages of the invention are apparent from this disclosure and the claims.

According to the present invention there is provided a process for the acid-catalyzed hydrolysis of an organic hydroperoxide which comprises conducting the hydrolysis in a reaction medium comprising essentially a low boiling, low molecular weight alcohol and/or sulfolane (polar solvent) and phenol.

COMPOUNDS OXIDIZED

The instant invention is applicable to the treatment of hydroperoxide-containing oxidation mixtures obtained by the oxidation of aromatic compounds having up to 30 carbon atoms and the general formula

wherein $R_1$ and $R_2$ are either a hydrogen, an alkyl, preferably a lower alkyl, or an aryl group or wherein $R_1$ and $R_2$ taken together form a cycloalkyl ring having from 4 to 7 carbon atoms; and wherein A is an alkyl cycloalkyl, aryl or substituted aryl group, with the substituent groups being one or more or mixture of alkyl, alkoxy, halogen, nitro, cyano or the like. The aryl group A may be either mononuclear, i.e., phenyl, or polynuclear, i.e., naphthyl, and the like. Specific examples of suitable compounds to be oxidized for use in the instant invention include toluene, ethylbenzene, isopropylbenzene, sec-butylbenzene, o-diisopropylbenzene, p-methoxy isopropylbenzene, p-chloro isopropylbenzene, p-nitro isopropylbenzene, p-cyano isopropylbenzene, cyclohexylbenzene, 1,4-dicyclohexylbenzene, cyclopentylbenzene, cycloheptylbenzene, diphenyl methane, 1-ethylnaphthalene, 1-isopropylnaphthalene, 1-cyclohexylnaphthalene, 1-(naphthyl)octadecane, 1-(2-naphthyl)octadecane, 1-(1-naphthyl)eicosane, isobutane and the like.

OXIDIZING CONDITIONS

Compounds represented in the above general formula are oxidized within a temperature range of from 25° to 250° C. and preferably from 60° to 160° C. The oxidation is carried out within a time range of from 10 minutes up to 5 days and preferably from 30 minutes up to 24 hours.

The oxidation reaction can be carried out with the use of essentially pure oxygen or mixtures of oxygen with inert gases can be employed. Air can also be used as the source of oxygen for the reaction according to this invention. The amount of oxygen employed is not particularly critical and can be in the range of from atmospheric pressure up to 5,000 psig of oxygen or preferably from 50 up to 500 psig of oxygen. If mixtures of oxygen with other gases are employed, the above figures refer to the partial pressure of oxygen in said mixtures, The oxidation reaction can be carried out simply by passing the oxygen containing gas through the compound being oxidized under the above described conditions or time, temperature and oxygen pressure. It is also within the scope of this invention to employ suitable oxidation initiators or catalysts which are known in the art. It is also possible to carry the oxidation reaction out in the presence of suitable amounts of base to neutralize acidic materials which may be formed as by-products in the oxidation reaction. This latter feature is also known in the art.

HYDROPEROXIDE EXTRACTION STEP

The oxidation reaction mixture prepared according to the reaction conditions described above is then generally subjected to an extraction step which separates the hydroperoxide from the oxidation mixture and places it in a suitable medium for the hydroperoxide decomposition conducted according to this invention described in detail below. Said hydroperoxide extraction is preferably carried out with a suitable amount of at least one of the solvent components which is to be employed in the hydroperoxide decomposition step. For example, methanol appears to be a particularly suitable extraction solvent for removing the hydroperoxide from the oxidation reaction mixture and providing a suitable solution for use in the hydroperoxide decomposition step described below. If desired, the hydroperoxide concentration in the extraction solvent can be adjusted by adding additional solvent or by distilling away a portion of the solvent employed in the extraction step.

HYDROPEROXIDE DECOMPOSITION STEP

According to the instant invention, a hydroperoxide formed by oxidation of an organic compound is subjected to an acid catalyzed decomposition in the presence of a mixture of phenol with a cosolvent or codiluent selected from methanol, sulfolane, ethanol, 1-propanol, 2-propanol, 1-butanol, and 2-butanol. Ethylene glycol was tried but results were quite inferior.

The acid employed for the hydroperoxide decomposition according to this invention can be characterized as a strong protonic acid. Such acids are well known in the art and include for example, sulfuric acid, arylsulfonic acids, e.g., p-toluenesulfonic acid, trifluoroacetic acid, trichloroacetic acid, trifluoromethanesulfonic acid, and the like. Said acids can be employed as aqueous solutions of suitable concentration, usually greater than 50% by weight. The amount of acid which is employed for the hydroperoxide decomposition can be expressed in terms of the hydroperoxide present in the reaction mixture. Broadly, the amount of acid employed can be from 0.001 up to 10 parts by weight of acid per 1 part by weight of hydroperoxide and preferably from 0.005 up to 1.0 parts by weight of acid per 1 part by weight of hydroperoxide in the reaction mixture.

The ranges of weight ratios of acid/phenol/cosolvent/hydroperoxide which can be employed include 0.001: 0.1: 0.5: 1 to 10: 50: 100: 1, preferably 0.005: 0.5: 1: 1 to 1.0: 10: 20: 1. Generally, the hydroperoxide content of the oxidation reaction mixture is from 0.02 to 0.99 parts by weight of hydroperoxide per 1 part by weight of the oxidation reaction mixture and preferably this amount is from 0.05 up to 0.70 parts by weight of hydroperoxide per 1 part by weight of the oxidation reaction mixture. Analytical methods for determining the hydroperoxide content in said oxidation reaction mixtures are well known in the art. As mentioned above, a particular feature of this invention involves the use of a mixture of phenol with a cosolvent as the reaction medium for the hydroperoxide decomposition.

I have found that cyclohexanone can be substituted for phenol in the reaction mixture for the hydroperoxide decomposition but that generally poorer results are obtained when this substitution is made. It is not *necessary* according to this invention that the hydroperoxide decomposition reaction mixture be essentially homogeneous and the reaction can be carried out in the presence of 2 or more phases in the reaction mixture. In any case, good mixing is desired to insure a rapid reaction as well as a safe reaction for the hydroperoxide decomposition.

The hydroperoxide decomposition according to the instant invention is carried out within a temperature range of from 0° C. up to 100° C. and preferably from 25° to 70° C. The reaction is carried out broadly for a time period of from 10 seconds up to 10 hours and preferably from 5 minutes up to 6 hours. The pressure employed in the hydroperoxide decomposition step is not critical.

SEPARATION AND NEUTRALIZATION STEPS

The use of aqueous strong acids such as those described above in the hydroperoxide decomposition step will usually mean that there will be an aqueous phase and an organic phase at the conclusion of the decomposition reaction. If there is only one phase present, suitable amounts of water can be added to form a separate aqueous phase containing most of the strong acid hydroperoxide decomposition catalyst and an organic phase containing essentially the decomposition products, which are not appreciably soluble in water. According to this invention, it is desirable to separate the aqueous phase containing the acid catalysts and return it to the hydroperoxide decomposition reaction zone. The remaining organic phase is neutralized with a suitable amount of base such as an alkali metal hydroperoxide or carbonate or an alkaline earth metal hydroxide or carbonate. Ammonia and amines can also be used as neutralizing bases for the organic phase. The amount of neutralizing base is not critical and can easily be determined by common analytical methods. Specifically, the amount of neutralizing base employed will at least be that amount to neutralize the acid present in the organic phase. Generally speaking, an excess of that amount required for this neutralization is usually employed for convenience in speeding up the neutralization reaction. Said organic phase which has been treated with base to neutralize the acid present is then generally filtered to remove insoluble salts and the like which may have formed on the neutralization. The filtrate can then be subjected to various known procedures for separating the products of the decomposition reaction. For example, an extractive distillation with sulfolane can be employed to separate phenol and cyclohexanone produced by the decomposition of cyclohexylbenzene hydroperoxide under the conditions broadly disclosed above. Other suitable means known in the art can be employed for separating phenol and the carbonyl containing compound from the above described mixtures.

EXAMPLE I

A series of runs were conducted according to the instant invention in which a solution of cyclohexylbenzene hydroperoxide in essentially unreacted cyclohexylbenzene was employed. In each run, the amount of sulfuric acid employed was 1% by weight based on the cyclohexylbenzene hydroperoxide in the reaction mixture. A small amount of amylbenzene (0.43 grams) was added to each reaction mixture as an internal standard for gas-liquid phase chromatography analyses to be conducted on the reaction mixture. Each run employed 4.0 grams of the cyclohexylbenzene hydroperoxide mixture which contained 1.08 grams of the cyclohexylbenzene hydroperoxide. The reaction time in each run was 2 hours. The diluents employed in each run and the results obtained for each run are presented below in Table 1.

Table I

| Run No. | Temp. °C. | Methanol, Grams | Phenol, Grams | Percent Yield(a) Cyclo-hexanone | Percent Yield(a) Phenol |
|---|---|---|---|---|---|
| 1 | 45 | 2 | 2 | 91 | 93 |
| 2 | 45 | 0 | 4 | 78 | 93 |
| 3 | Reflux (~65) | 2 | 0 | 40 | 64 |
| 4 | 45 | 2 | 1.06 | 95 | 98 |
| 5 | 45 | 2 | 0.26 | 68 | 57 |
| 6 | 45 | 2 | 0 | 48 | 47 |
| 7 | 45 | 1.5 | 0 | 40 | 48 |

(a)Yields are calculated based on the amount of cyclohexylbenzene hydroperoxide charged to the reaction mixture.

The results of the above runs demonstrate that a much improved yield of cyclohexanone and phenol can be obtained according to the instant invention when a mixture of phenol and methanol are employed as the diluent for the hydroperoxide decomposition reaction (Run 1 and Run 4).

Viewing the data herein it is now believed that the amount of phenol present in the reaction mixture will have a significant effect on the quantities of products yielded. Viewing especially Runs 1, 4, and 5, it appears that up to a certain level the phenol increases the effective acidity. Above this, side reactions involving coproducts of cyclohexanone and phenol appear to reduce the yields of these two compounds.

none and phenol in this run is about 75% of theoretical based on the amount of cyclohexylbenzene hydroperoxide employed in the run.

Runs were made to determine the effect on the solvent system of the invention when replacing the alcohol with sulfolane. Results are in Table II.

Table II

| | Cleavage of Cyclohexylbenzene Hydroperoxide to Phenol & Cyclohexanone[a] | | | | | | |
|---|---|---|---|---|---|---|---|
| Run No. | Oxid. Product (g) | Solvents (g) | Phenol (g) | Solvent-$H_2SO_4$ g. | g. | Yield Cyclohexanone mol % | Phenol mol % |
| 1[b] | 10 | 4, Sulfolane | 1.6 | 1.0 | 0.0169 | 73 | 77 |
| 2[b] | 10 | 4, Sulfolane | — | 1.0 | 0.0169 | 64 | 67 |

[a] The cleavage was carried out at 45° C., for 2 hours
[b] Oxidation products contained 13.19 wt. % Hydroperoxide.

EXAMPLE II

Cyclohexylbenzene (100 grams) was oxidized in the presence of 1.0 grams of cumene hydroperoxide and 0.05 grams of sodium carbonate at 115° C. for 3 hours and 46 minutes. The reaction was carried out in a 300 ml autoclave under oxygen pressure which was initially 328 psig and decreased to 160 psig during the course of the run. Analysis of the reaction mixture indicated a cyclohexylbenzene hydroperoxide content of 15.7 weight percent. A portion (90 grams) of the above reaction mixture was mixed with 90 grams of methanol and 9 grams of water in a separatory funnel and there was obtained a cyclohexylbenzene layer which weighed 63.80 grams. This layer was mixed with an additional 63.8 grams of methanol and 6.38 grams of water. From this mixture another cyclohexylbenzene layer of 48.94 grams was obtained and a methanol layer which was combined with the original methanol phase from the first mixture. The second cyclohexylbenzene layer was treated to evaporate a small amount of methanol and water contained therein to give 47.72 grams of cyclohexylbenzene which contained 0.87 grams or about $4.5 \times 10^{-3}$ moles of cyclohexylbenzene hydroperoxide. The methanol layers mentioned above were evaporated at 50° C. under vacuum to obtain 41.40 grams of material which contained the cyclohexylbenzene hydroperoxide. A portion of this mixture (35 grams) was mixed with 10 grams of phenol and 17.5 grams of methanol in a 200 ml flask. The solution was kept in a constant temperature bath at 50° C. An acid solution containing 1.30 grams of phenol, 0.15 grams of 97% sulfuric acid was added dropwise to the cyclohexylbenzene solution. After 2.5 hours reaction, the reaction mixture was neutralized by addition of 0.26 grams of sodium bicarbonate. After the mixture was stirred for 10 minutes, the mixture was then distilled. The first fraction obtained was methanol which contained 0.22 grams of cyclohexanone, 0.382 grams of phenol and 0.971 grams of cyclohexylbenzene. The second fraction was recovered from the mixture in about 25 minutes distillation time by using higher heating on the distillation vessel. This fraction weighed 42.5 grams and was redistilled in a smaller flask (100 ml) to obtain 3 fractions therefrom. Fraction A weighed 19.58 grams, Fraction B, 1.26 grams, and Fraction C, 19.24 grams. Each fraction as well as material collected in the distillation traps was analyzed by gas-liquid phase chromatography to reveal the amount of cyclohexanone, phenol and cyclohexylbenzene present in the mixture. The analyses revealed that there was recovered 3.71 grams of cyclohexanone, a net production of 4.78 grams of phenol, and 21.54 grams of cyclohexylbenzene. The yield of cyclohexa- The procedure employed to obtain the results of Table II was as follows.

The oxidation product and solvents were mixed in a 25 ml Erlenmeyer flask which was equipped with a magnetic stirrer. The mixture was then heated up to 45° C. by using water bath. Sulfuric acid which dissolves in the solvent was added slowly into the mixture. The final mixture was then heated at 45° C. for 2 hours. The cleavage products were analyzed by Gas Chromatography.

Reasonable variation and modification are possible within the scope of the foregoing disclosure and the claims to the invention the essence of which is that an organic hydroperoxide is by acid-catalysis, hydrolyzed in a reaction medium comprising essentially a mixture of polar solvent, e.g., a low boiling, low molecular weight alcohol and/or sulfolane together with phenol.

I claim:

1. A process for the acid-catalyzed hydrolysis of an organic hydroperoxide which comprises conducting the hydrolysis in a reaction medium comprising phenol and at least one material selected from a low boiling or low molecular weight alcohol and sulfolane.

2. A process according to claim 1 wherein the alcohol is selected from methanol, ethanol, 1-proponal, 1-butanol and 2-butanol.

3. A process according to claim 1 whenever the medium contains sulfolane.

4. A process according to claim 1 wherein the organic hydroperoxide is a naphthene hydroperoxide.

5. A process according to claim 1 wherein the alcohol is methanol and the hydroperoxide is a naphthene hydroperoxide.

6. A process according to claim 1 wherein the hydroperoxide is cyclohexylbenzene hydroperoxide.

7. A process according to claim 1 wherein the alcohol is methanol and the hydroperoxide is cyclohexylbenzene hydroperoxide.

8. A process for the production of cyclohexanone and phenol from cyclohexylbenzene which comprises converting cyclohexylbenzene to cyclohexylbenzene hydroperoxide and then hydrolyzing the hydroperoxide in the presence of a reaction medium comprising essentially phenol and at least one of a low boiling, low molecular weight alcohol and sulfolane, under conditions to obtain said cyclohexanone and said phenol.

9. A process according to claim 8 wherein the conversion of the cyclohexylbenzene hydroperoxide is effected in the presence of sulfolane and phenol.

10. A process according to claim 8 wherein the conversion of the cyclohexylbenzene hydroperoxide is effected in the presence of a low boiling, low molecular weight alcohol.

11. A process according to claim 1 wherein the organic hydroperoxide is obtained by the oxidation of an aromatic compound having up to 30 carbon atoms and having the general formula

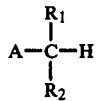

wherein $R_1$ and $R_2$ is selected from hydrogen, alkyl, aryl, and $R_1$ and $R_2$ taken together forming a cycloalkyl ring having 4–7 carbon atoms; and wherein A is selected from alkyl, cycloalkyl, aryl, and substituted aryl.

12. A process according to claim 1 wherein the organic hydroperoxide is obtained by the oxidation of an aromatic compound having up to 30 carbon atoms and the general formula

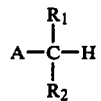

wherein $R_1$ and $R_2$ together form a cycloalkyl ring having 4–7 carbon atoms and A is selected from aryl and cycloalkyl groups.

* * * * *